United States Patent
Klee et al.

(10) Patent No.: US 9,775,786 B2
(45) Date of Patent: Oct. 3, 2017

(54) DENTAL ADHESIVE

(71) Applicant: DENTSPLY INTERNATIONAL iNC., York, PA (US)

(72) Inventors: Joachim E Klee, Radolfzell (DE); Uwe Lehmann, Constance (DE)

( * ) Notice: Subject to any disclaimer, the term of this patent is extended or adjusted under 35 U.S.C. 154(b) by 0 days.

(21) Appl. No.: 14/580,893

(22) Filed: Dec. 23, 2014

(65) Prior Publication Data
US 2015/0335535 A1     Nov. 26, 2015

Related U.S. Application Data

(63) Continuation of application No. 14/331,349, filed on Jul. 15, 2014, now abandoned, which is a continuation of application No. 12/148,568, filed on Apr. 21, 2008, now abandoned.

(51) Int. Cl.
    *A61K 6/083*     (2006.01)
    *C08L 43/02*     (2006.01)
    *A61K 6/00*     (2006.01)

(52) U.S. Cl.
    CPC .......... *A61K 6/0029* (2013.01); *A61K 6/0023* (2013.01)

(58) Field of Classification Search
    USPC ............................... 523/116, 118; 433/228.1
    See application file for complete search history.

(56) References Cited

U.S. PATENT DOCUMENTS

| | | | | |
|---|---|---|---|---|
| 2,741,563 A * | 4/1956 | Robertson | ............ | C08K 5/092 106/270 |
| 5,320,886 A | 6/1994 | Bowen | | |
| 5,401,783 A | 3/1995 | Bowen | | |
| 6,071,982 A | 6/2000 | Wise et al. | | |
| 6,486,232 B1 | 11/2002 | Wise et al. | | |
| 6,583,248 B1 * | 6/2003 | Bowen | ................ | A61K 6/0023 525/328.2 |
| 6,812,266 B2 | 11/2004 | Klee et al. | | |
| 7,078,451 B2 * | 7/2006 | Hartman | ................. | C08K 3/22 523/514 |
| 8,198,388 B2 * | 6/2012 | Klee | ................... | A61K 6/0023 522/171 |
| 2007/0293642 A1 * | 12/2007 | Klee | ................... | A61K 6/0023 526/193 |

FOREIGN PATENT DOCUMENTS

| | | |
|---|---|---|
| EP | 1548021 A1 | 6/2005 |
| WO | 0248213 A1 | 6/2002 |
| WO | 2007045303 A1 | 4/2007 |

OTHER PUBLICATIONS

European search report, Application No. 05022930.1, dated Mar. 17, 2006.

* cited by examiner

*Primary Examiner* — Tae H Yoon
(74) *Attorney, Agent, or Firm* — McNees Wallace & Nurick LLC

(57) ABSTRACT

A one-part self-etching, self-priming dental adhesive having a pH of at most 2, which comprises an aqueous mixture containing (i) one or more polymerizable monomers optionally containing an acidic group,
(ii) optionally one or more organic or inorganic acids,
(iii) a polymerization initiator, and
(iv) a thermal polymerisation inhibitor of the following formula (I):

$$\begin{array}{c} OR'_1 \\ \diagup\!\!\diagdown \\ | \quad |\text{—}(R'_2)_c \\ \diagdown\!\!\diagup \\ OH \end{array}$$

wherein
$R'_1$ represents
    a hydrogen atom, or a saturated hydrocarbon group having 1 to 18 carbon atoms.
$R'_2$, which may be the same or different if more than one $R'_2$ is present, independently represent
    a saturated hydrocarbon group having 1 to 18 carbon atoms, and
c represents an integer of from 1 to 4.

12 Claims, 6 Drawing Sheets

DENTAL ADHESIVE

REFERENCE TO RELATED APPLICATIONS

This application is a continuation of U.S. patent application Ser. No. 14/331,349, filed Jul. 15, 2014 and entitled "Dental Adhesive", now abandoned, which is a continuation of U.S. patent application Ser. No. 12/148,568, filed Apr. 21, 2008 and entitled "Dental Adhesive", now abandoned, which claims priority to PCT/EP2006/008612, filed Sep. 4, 2006 and entitled "Dental Adhesive", which claims priority to EP05022930.1, filed Oct. 20, 2005, entitled "Dental Adhesive".

FIELD OF THE INVENTION

The present invention relates to a one-part self-etching, self-priming dental adhesive having improved storage stability and low toxicity. Moreover, the present invention also relates to the use of a specific thermal polymerisation inhibitor in a one-part self-etching, self-priming dental adhesive having a pH of at most 2.

BACKGROUND OF THE INVENTION

One-part self-etching, self-priming dental adhesive compositions known from the prior art typically contain a mixture of an acid, a polymerizable monomer and an initiator system in a suitable solvent. The acidity of the mixture must be adapted to provide sufficient etching activity on dentin and enamel surfaces. However, an increased acidity leads to a complex stability problem due to the activation of chemical bonds of the functional components of the mixture. Specifically, ester bonds present in the polymerizable monomers may be solved under acid catalysis. Moreover, the initiator system may be activated in the acidic medium leading to premature polymerization of the mixture.

As a result of the stability problem of the mixture, the storage stability at room temperature of commercial one-part self-etching, self-priming dental adhesive compositions known from the prior art may be insufficient. Accordingly, conventional commercial one-part self-etching, self-priming dental adhesive compositions must be stored in a refrigerator in order to avoid deterioration by solvolysis or polymerization. As an Example, the commercial composition "iBond Gluma inside" may be mentioned, which has a low thermal stability when stored at temperatures of 37° C. or 50° C. due to premature polymerization within less than two weeks, which is indicative of an insufficient thermal stability at room temperature for all practical purposes.

EP-A 1 548 021 suggests hydrolysis stable one-part self-etching, self-priming dental adhesive compositions containing specific monomers having improved resistance against hydrolysis under acidic conditions. In order to improve the stability of the initiator system, EP-A 1 548 021 suggests a stabilizer such as hydroquinone monomethylether, 2,6-di-tert.-butyl-p-cresol, tetramethyl piperidine N-oxyl radical and galvanoxyl radical. However, generic one-part self-etching, self-priming dental adhesive composition known from EP-A 1 548 021 still require improvement of the thermal stability at storage for attaining a stability of at least 10 days at 60° C. required. Moreover, hydroquinone is an allergenic compound imparting undesirable toxic properties to a dental adhesive composition.

SUMMARY OF THE INVENTION

It is a problem of the present invention to provide a one-part self-etching, self-priming dental adhesive composition having a low toxicity and thermal stability at storage of at least 10 days at 60° C.

The present invention provides a one-part self-etching, self-priming dental adhesive having a pH of at most 2, which comprises an aqueous mixture containing
(i) one or more polymerizable monomers optionally containing an acidic group,
(ii) optionally one or more organic or inorganic acids,
(iii) a polymerization initiator, and
(iv) a thermal polymerisation inhibitor of the following formula (I):

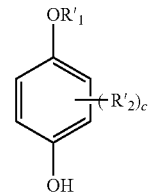

wherein
R'$_1$ represents
    a hydrogen atom, or a saturated hydrocarbon group having 1 to 18 carbon atoms.
R'$_2$, which may be the same or different if more than one R'$_2$ is present, independently represent
    a saturated hydrocarbon group having 1 to 18 carbon atoms, and
c represents an integer of from 1 to 4.

The present invention is based on the recognition that an aqueous mixture containing one or more polymerizable monomers optionally containing an acidic group, one or more organic or inorganic acids, and a polymerization initiator is particularity problematic with regard to polymerization whereby conventional stabilizers such as hydroquinone monomethylether, 2,6-di-tert.-butyl-p-cresol, tetramethyl piperidine N-oxyl radical and galvanoxyl radical provide an insufficient effect for attaining a high storage stability.

The present invention is furthermore based on the recognition that a specific class of water insoluble stabilizers provides a surprising stabilizing effect in an acidic aqueous mixture so that a one-part self-etching, self-priming dental adhesive having a pH of at most 2 may be provided which has an excellent storage stability due to an improved resistance against premature polymerization.

Accordingly, the present invention also relates to the of a thermal polymerisation inhibitor of formula (I) in a one-part self-etching, self-priming dental adhesive having a pH of at most 2.

DESCRIPTION OF THE PREFERRED EMBODIMENTS

Figure 1:
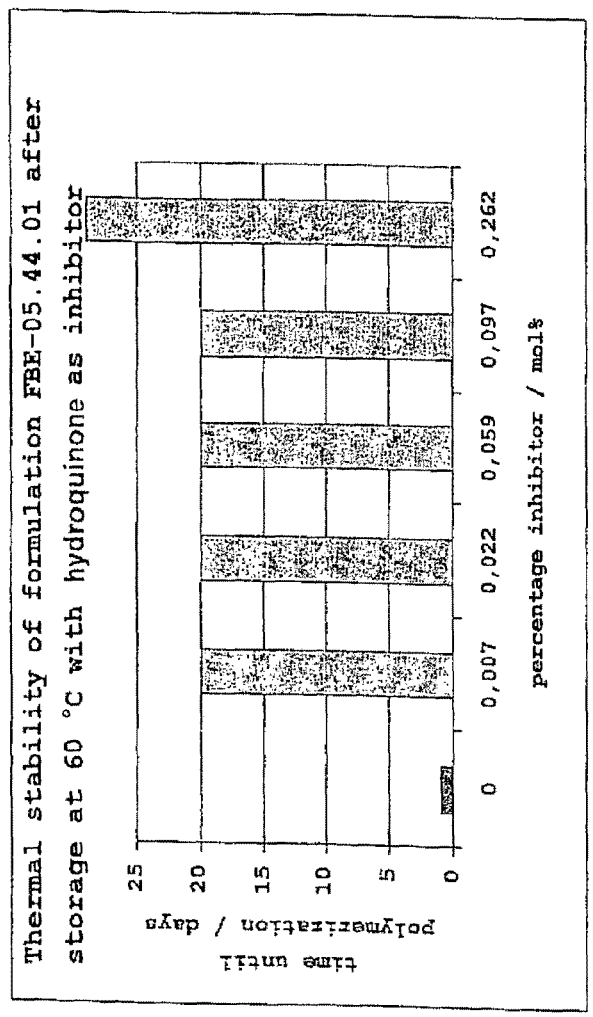
FIG. 1 shows the thermal stability of formulation FBE-05.44.01 after storage at 60° C. with hydroquinone (HQ) as inhibitor.

The dental adhesive composition according to the present invention contains a water-insoluble thermal polymerisation inhibitor of formula (I).

Preferably, the saturated hydrocarbon group which may be present as $R'_1$ or $R'_2$ in formula (I) represents a straight chain or branched $C_{1-18}$, alkyl group or a $C_{3-8}$ cycloalkyl group optionally substituted by one or more $C_{1-5}$ alkyl groups or a $C_{4-18}$ cycloalkylalkyl group optionally substituted by one or more $C_{1-5}$ alkyl groups.

Preferably, $R'_1$ represents a straight chain or branched $C_{1-18}$ alkyl group. In a preferred embodiment, $R'_1$ is hydrogen or a tert.-butyl group.

$R'_2$ in formula (I) is believed to provide a steric effect due to the bulky nature of the substituent in this position. Therefore, at least one $R'_2$ in formula (I) is a saturated hydrocarbon group having 1 to 18 carbon atoms. Accordingly, in a specific embodiment, at least one $R'_2$ in formula (I) represents a branched $C_{3-18}$ alkyl group or a $C_{3-18}$ cycloalkyl group optionally substituted by one or more $C_{1-5}$ alkyl groups or a $C_{4-18}$ cycloalkylalkyl group optionally substituted by one or more $C_{1-5}$ alkyl groups. More specifically, at least one $R'_2$ in formula (I) preferably represents a branched $C_{3-18}$ alkyl group or a $C_{3-18}$ cycloalkyl group optionally substituted by one or more $C_{1-5}$ alkyl groups. Even more specifically, at least one $R'_2$ in formula (I) preferably represents a branched $C_{3-18}$ alkyl group. In a further preferred embodiment, $R'_2$ is a tert.-butyl group.

c represents an integer of from 1 to 4, preferably 1 or 2. In a specific embodiment, c is 1.

Most preferably, the inhibitor is tert.-butyl hydroquinone (TBHQ) or tert.-butyl hydroxyanisole (BHA).

Preferably, the inhibitor is contained in the dental adhesive composition in an amount of from 0.01 to 0.5 mol %, more preferably in an amount of from 0.05 to 0.3 mol %.

In a preferred embodiment, The present invention provides a one-part self-etching, self-priming dental adhesive having a pH of at most 2, which comprises an aqueous mixture containing
(i) one or more polymerizable monomers optionally containing an acidic group,
(ii) optionally one or more organic or inorganic acids,
(iii) a polymerization initiator, and
(iv) a thermal polymerisation inhibitor of the following formula:

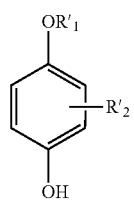

wherein $R'1$ represents a hydrogen atom, or a saturated hydrocarbon group having 1 to 18 carbon atoms.

$R'_2$ represents a saturated hydrocarbon group having 1 to 18 carbon atoms.

The dental adhesive composition according to the present invention contains polymerizable monomers optionally containing an acidic group. Preferably, the polymerizable monomer is a polymerizable acidic phosphoric acid ester monomer of the following formula (A):

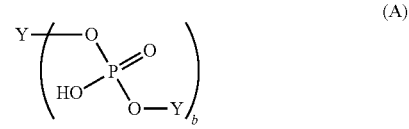

wherein the moieties Y independent from each other represent a hydrogen atom or a moiety of the following formula (Y)

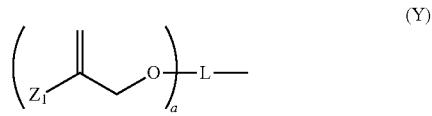

wherein $Z_1$ is $COOR^{10}$, $COSR^{20}$, $CON(R^{10})_2$, $CONR^{10}R^{20}$, or $CONHR^{10}$, wherein $R^{10}$ and $R^{20}$ independently represent a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$, aryl or heteroaryl group, an optionally substituted $C_{5-18}$ alkylaryl or alkylheteroaryl group, or an optionally substituted $C_{7-30}$ aralkyl group, whereby two $R_1$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s); L represents an (a+b)-valent organic residue (whereby b is 1 when Y in formula (A) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl) acryl derivative group; a is an integer of from 1 to 10, preferably 1 to 5; b is an integer of from 1 to 10, preferably 1 to 5; provided that at least one Y is not hydrogen. The preparation of such monomers is known from EP-A 1 548 021.

The dental adhesive may also contain polymerisable acidic monomers selected from the group consisting of
(b1) polymerisable acidic monomers of the following formula (B):

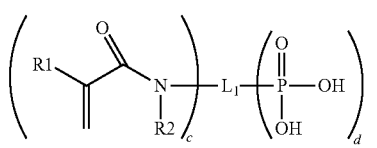

(B)

wherein R₁ and R₂ independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylh3eteroaryl group, an optionally substituted $C_{7-30}$ aralkyl group, whereby the optionally substituted groups may be substituted by 1 to 5 $C_{1-5}$ alkyl group(s);

$L_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of said c+d carbon atoms linking a phosphonate or optionally substituted acrylamido group; and c and d independently represent integers of from 1 to 10;

(b2) polymerisable acidic monomers of the following formula (C):

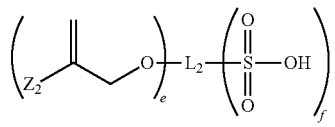

(C)

wherein $Z_2$ independently has the same meaning as defined for $Z_1$;

$L_2$ represents an (e+f) valent organic residue containing 2 to 45 carbon atoms and optionally heteroatoms such as oxygen, nitrogen and sulfur-atoms, the carbon atoms including e+f carbon atoms selected from primary and secondary aliphatic carbon atoms, secondary alicyclic carbon atoms, and aromatic carbon atoms, each of said e+f carbon atoms linking a sulphonate or optionally substituted 2-(oxa-ethyl)acryl derivative group; and e and f independently represent an integer of from 1 to 10;

(b3) acidic monomers of the following formula (D):

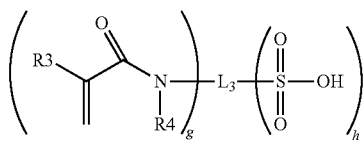

(D)

wherein

R₃ and R₄ independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s) $L_3$ represents a (g+h) valent organic residue containing 2 to 45 carbon atoms and optionally heteroatoms such as oxygen, nitrogen and sulfur atoms, the carbon atoms including g+h carbon atoms selected from primary and secondary aliphatic carbon atoms, secondary alicyclic carbon atoms, and aromatic carbon atoms, each of said g+h carbon atoms linking a sulphonate or optionally substituted acrylamido group; and g and h independently represent integers of from 1 to 10.

In a preferred embodiment, the dental adhesive contains a polymerizable monomer characterized by one of the following formulas:

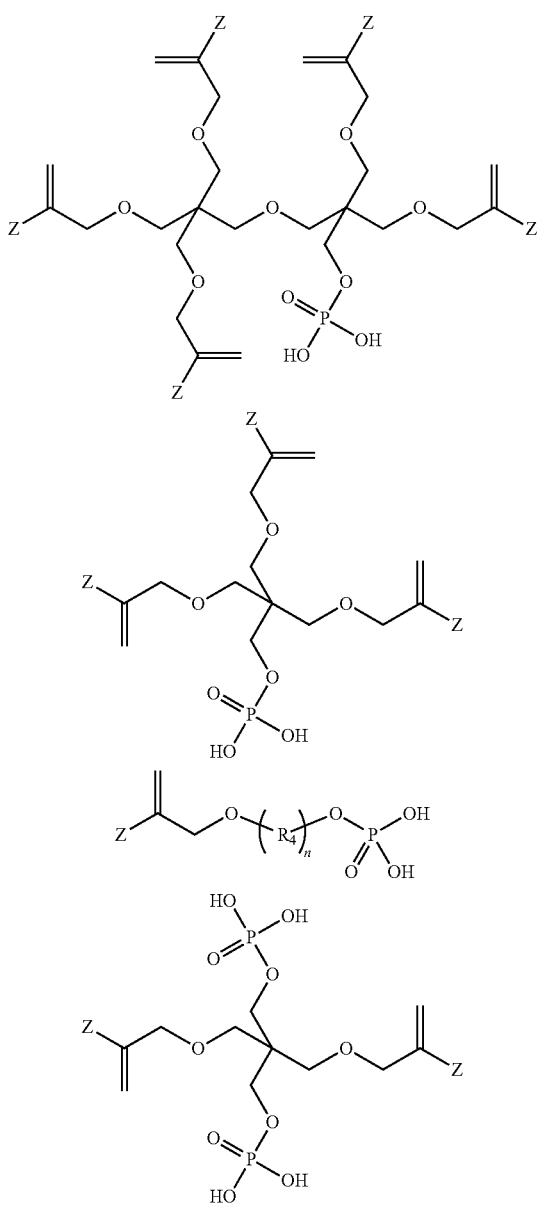

wherein Z is $Z_1$ as defined above, $(R_4)$ is an optionally substituted alkylene group, and n is an integer.

In a further preferred embodiment, the dental adhesive contains a polymerizable monomer characterized by one of the following formulas:

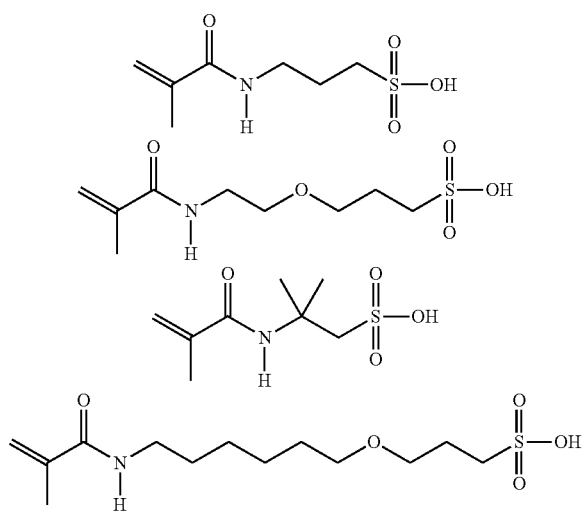

In a still further preferred embodiment, the dental adhesive contains a polymerizable monomer characterized by one of the following formulas:

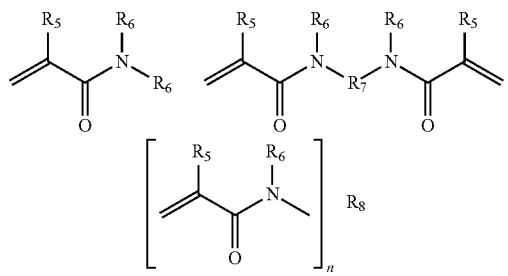

wherein $R_5$ and $R_6$ independently represent a hydrogen atom or a substituted, a $C_1$ to $C_{18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, $R_7$ represents a divalent substituted or unsubstituted organic residue having from 1 to 45 carbon atoms, whereby said organic residue may contain from 1 to 14 oxygen and/or nitrogen atoms and is selected from a $C_1$ to $C_{18}$ alkylene group wherein from 1 to 6 —$CH_2$— groups may be replaced by a —N—(C=O)—$CR_9$=$CH_2$ group wherein $R_9$ is a hydrogen atom or a $C_1$ to $C_{18}$ alkyl group, a divalent substituted or unsubstituted $C_3$ to $C_{18}$ cycloalkyl or cycloalkylene group, a divalent substituted or unsubstituted $C_4$ to $C_{18}$ aryl or heteroaryl group, a divalent substituted or unsubstituted $C_5$ to $C_{18}$ alkylaryl or alkylheteroaryl group, a divalent substituted or unsubstituted $C_7$ to $C_{30}$ aralkyl group, and a divalent substituted or unsubstituted $C_2$ to $C_{45}$ mono-, di- or polyether group having from 1 to 14 oxygen atoms, $R_8$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_2$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and n is an integer.

The dental adhesive may also contain a mono-, bis- or poly(meth)acrylamide characterized by one of the following formulas:

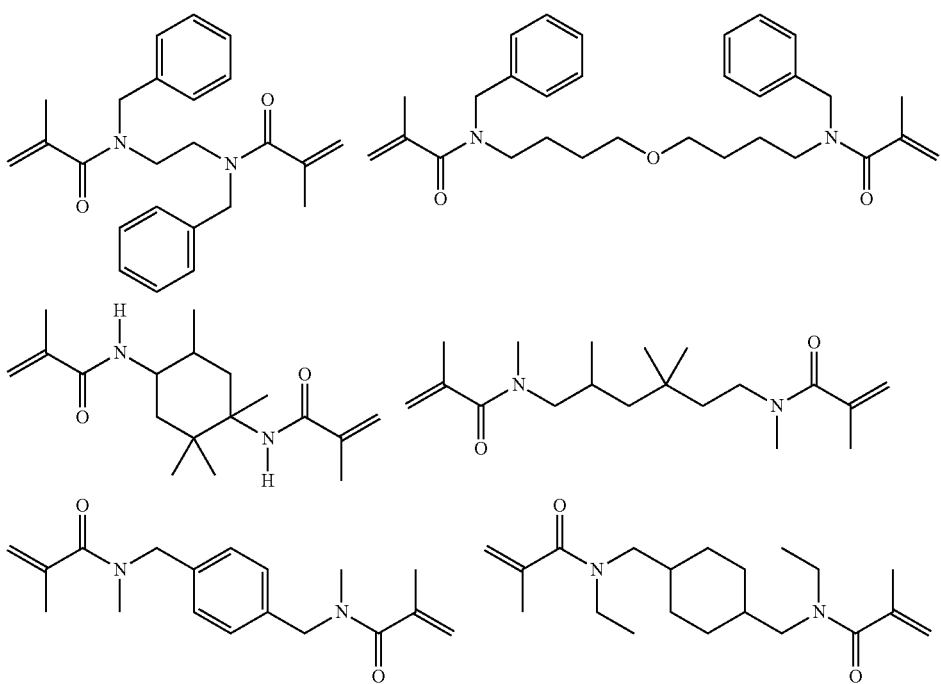

-continued

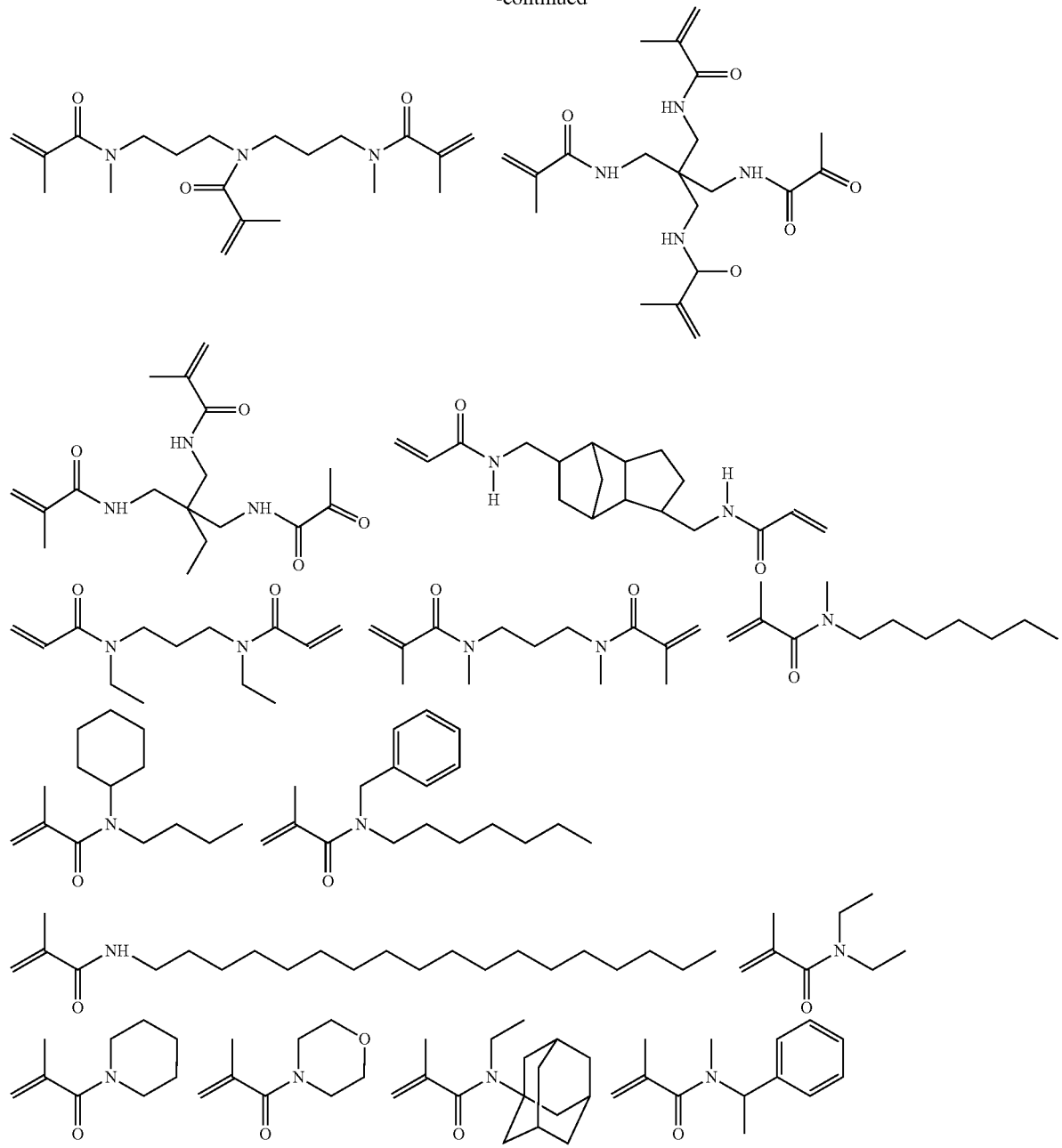

The dental adhesive may also contain acrylic acid or methacrylic acid as polymerizable monomers containing an acidic group.

The dental adhesive according to the present invention may contain polymerizable monomers in an amount of from 5 to 90 wt-%, preferably in an amount of from 20 to 70 wt. %.

The aqueous mixture may further contain an organic water soluble solvent selected from the group of alcohols and ketones such as ethanol, propanol, butanol, acetone, methyl ethyl ketone.

A dental composition according to the present invention may include further acids whereby the pH of the composition may be easily adjusted. Examples of suitable acids are sulfuric acid, phosphoric acid, hydrochloric acid and the like. In a specific example, a further acid which is not-polymerizable is added for adjusting the pH.

The polymerization initiator may be a photo initiator such as camphor quinone.

The dental adhesive may further contain an inorganic filler and/or an organic filler; preferably the filler is a nanofiller.

A one-pack composition means that the composition of the present invention is contained in only one container which may be stored and allows application of the composition without any mixing and without any special equipment before the application.

Self-etching means that the dental adhesive composition of the present invention may be applied to a tooth without any preliminarily etching of enamel in a separate method step. Particularly, the polymerizable phosphoric acid ester derivative of the present invention allows the preparation of a dental composition which is hydrolysis stable for at least one week at a storage temperature of 50° C., whereby after such storage the bond strength of an adhesive prepared from such a dental composition to enamel and/or dentin is at least 10 MPa, preferably 15 MPa. Due to the high thermal stability of the composition of the present invention a one-part self-etching and self-priming system which has excellent shelf-life may be prepared.

The invention will now be further illustrated with reference to the following examples

EXAMPLES

Test Formulation containing different inhibitors.

A series of test formulations containing different thermal polymerization inhibitors was prepared in order to illustrate the surprising thermal stability of a dental adhesive composition according to the present invention. The standard composition was used as shown in Table 1.

TABLE 1

| Component | Content (wt.-%) |
| --- | --- |
| BAP | 63.156 |
| BAA-TCD | 21.052 |
| DHPOBA analog | 5.415 |
| 2-Acrylamido-2-methyl-propanesulfonic acid (AMPS) | 4.375 |
| Camphor Quinone | 1.282 |
| TPO | 3.229 |
| DMABE | 1.491 |
| Total | 100.000 |
| Active Matrix | 55 |
| Acrylic acid | 9 |
| Water | 36 |
| Total | 100 |

The following comparative inhibitors were tested:

(i) hydroquinone (HQ), (ii) hydroquinone monomethylether (HQME), (iii) Bisphenol A, (iv) Propyl gallate (PG)

The following inhibitors according to the present invention were tested:

(vii) tert-Butylhydroquinone (TBHQ), and (viii) tert.-Butylhydroxyanisol (BHA).

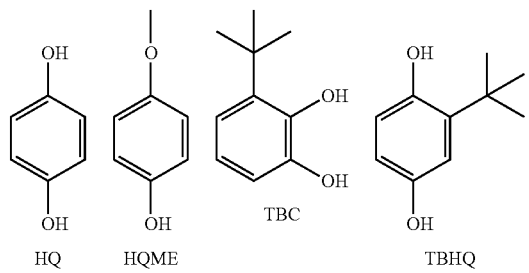

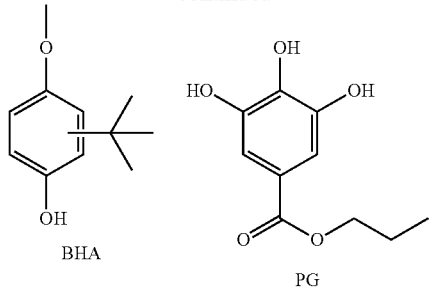

Test formulations containing different inhibitors or inhibitor concentrations were stored in Prime&Bond NT bottles (Dentsply DeTrey) at 60° C. until thermal polymerization. The bottles were daily examined by shaking the bottle, whereby the acoustical test turned out to be rather sensitive, and by taking a sample with a pipette. When polymerization seemed to have occurred or after a certain minimum storage time (20 days) the bottles were sliced open and the solution were examined visually.

According to the results of the above described Arrhenius investigation at least a thermal stability of about 11 days at 60° C. is necessary so that the dental adhesive composition may be stored at room temperature.

Results

The Test Formulation containing different inhibitors in different amounts, was investigated regarding its thermal stability by storing these formulations at 60° C. The samples were daily examined. In case of polymerization a gel or a solid, polymerized body was observed.

The dark shaded columns represent formulations with inhibitors, respectively inhibitor concentrations, which were polymerized after the depicted time at 60° C. The light shaded columns represent formulations, which were not polymerized until the depicted time. Usually after 20 days the investigation was terminated.

In the comparison, hydroquinone (HQ) was used in an amount of 0.15 mol % showing some stabilization effect. However, hydroquinone is an allergenic compound and therefore undesirable for use in a generic dental composition. Hydroquinone monomethylether (HQME) as well as BHT failed to provide a sufficient thermal stability.

(i) Hydroquinone (HQ)—Reference Inhibitor

FIG. 1 shows the thermal stability 10 of formulation FBE-05.44.01 after storage at 60° C. with hydroquinone (HQ) as the inhibitor. The light shaded columns indicate the formulation is not polymerised up to the recorded time. The dark shaded column indicates the formulation is polymerized after the recorded time.

(ii) Hydroquinone Monomethylether (HQME)—Reference Inhibitor

Figure 2:
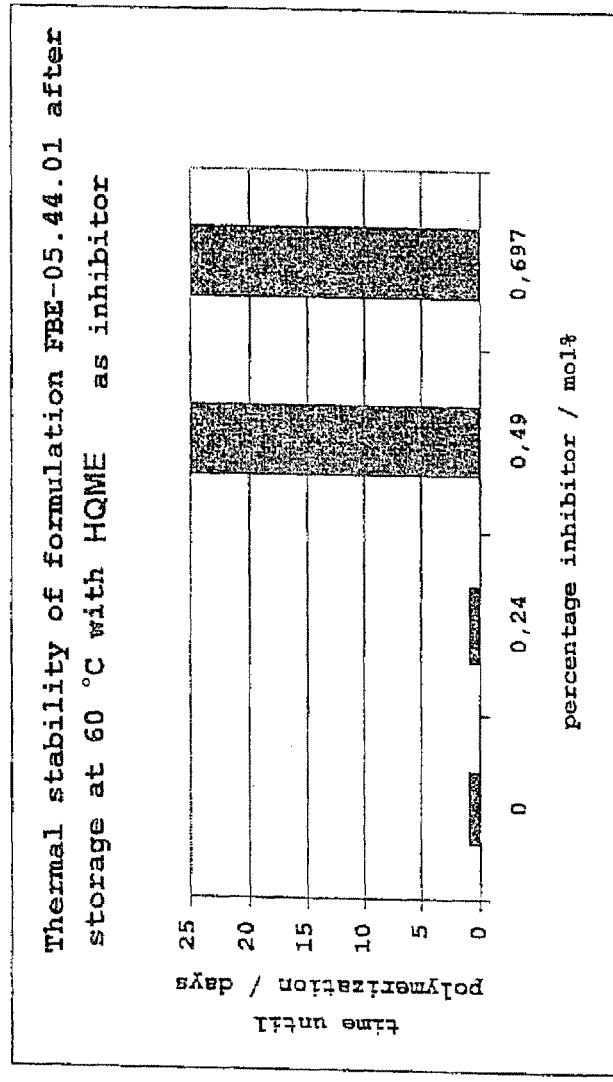
FIG. 2 shows the thermal stability of formulation FBE-05.44.01 after storage at 60° C. with hydroquinone monomethylether (HQME) as inhibitor

FIG. 2 shows the thermal stability 20 of formulation FBE-05.44.01 after storage at 60° C. with hydroquinone monomethylether (HQME) as the inhibitor.

After slicing open the samples containing 0.49 and 0.697 mol % HQME, small pieces of gel were found at the bottom, which were not detected before by shaking or by the examination with the pipette.

After slicing open the sample with 0.193 mol % TBC some pieces of gel were found at the bottom, which were not detected before by shaking or by the examination with the pipette.

(iii) Bisphenol A—Reference Inhibitor

Figure 3:
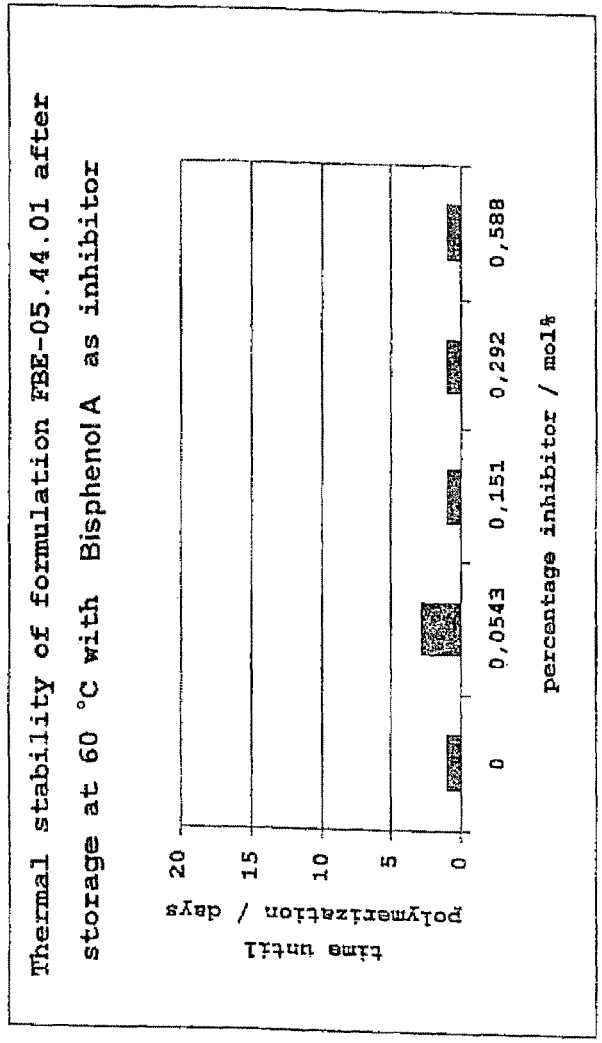
FIG. 3 shows the thermal stability of formulation FBE-05.44.01 after storage at 60° C. with Bisphenol A as inhibitor

FIG. 3 shows the thermal stability 30 of formulation FBE-05.44.01 after storage at 60° C. with Bisphenol A as the inhibitor. The dark shaded columns indicate that the formulation is polymerized after the recorded time.

(iv) Propyl Gallate (PG)—Reference Inhibitor

Figure 4:
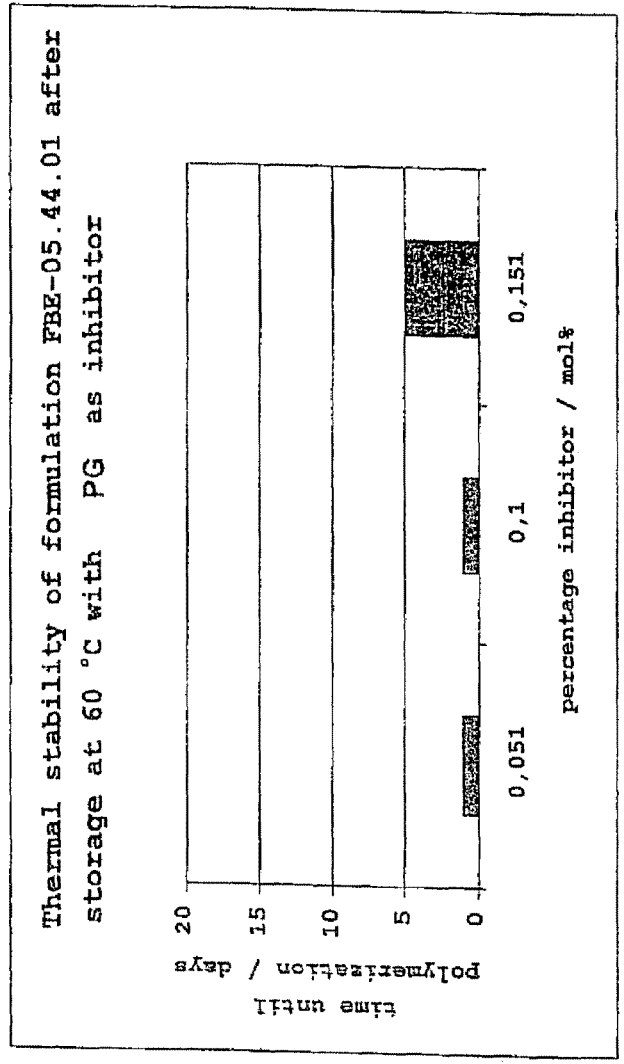
FIG. 4 shows the thermal stability of formulation FBE-05.44.01 after storage at 60° C. with propyl gallate (PG) as inhibitor.

FIG. 4 shows the thermal stability 40 of formulation FBE-05.44.01 after storage at 60° C. with propyl gallate (PG) as the inhibitor. The dark shaded columns indicate that the formulation is polymerized after the recorded time.

(v) tert.-Butylhydroquinone (TBHQ)—Inhibitor of the Invention

Figure 5:
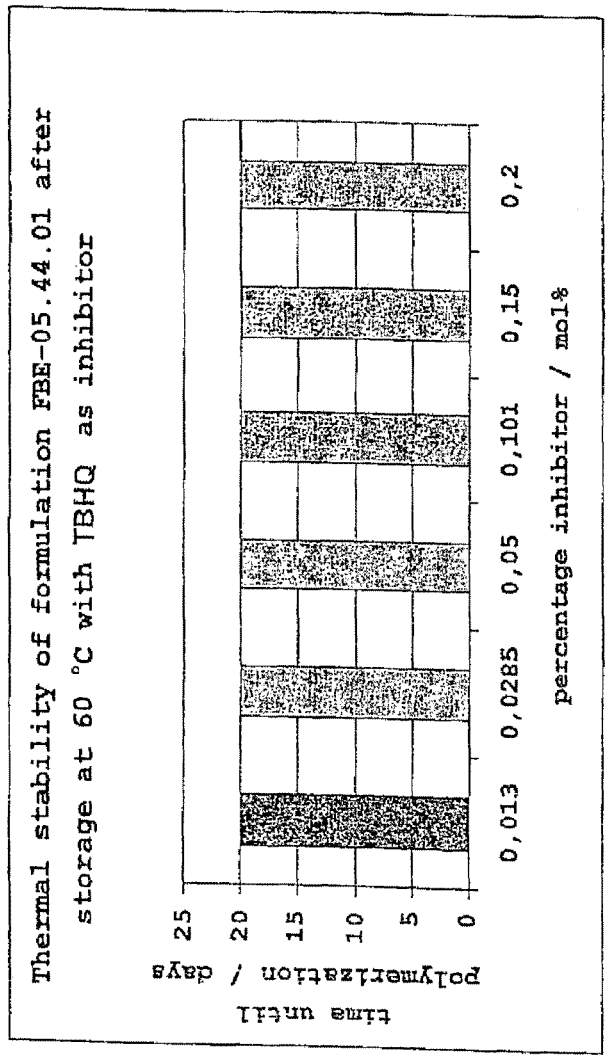
FIG. 5 shows the thermal stability of formulation FBE-05.44.01 after storage at 60° C. with tert.-butyl hydroquinone (TBHQ) as inhibitor.

FIG. 5 shows the thermal stability 50 of formulation FBE-05.44.01 after storage at 60° C. with tert.-butyl hydroquinone (TBHQ) as the inhibitor.

After 14 days and after 20 days at 60° C. the bottles were sliced open, the contents was investigated and filled in a new bottle, which was stored again at 60° C. No hints of a polymerization were found.

After 20 days at 60° C. the bottles were sliced open again and the contents was investigated. Only in case of the lowest TBHQ percentage of 0.013 mol % polymerization was found. This was not detected before by the daily examination.

(vii) tert.-Butylhydroquinone (TBHQ)—Inhibitor of the Invention

Figure 6:
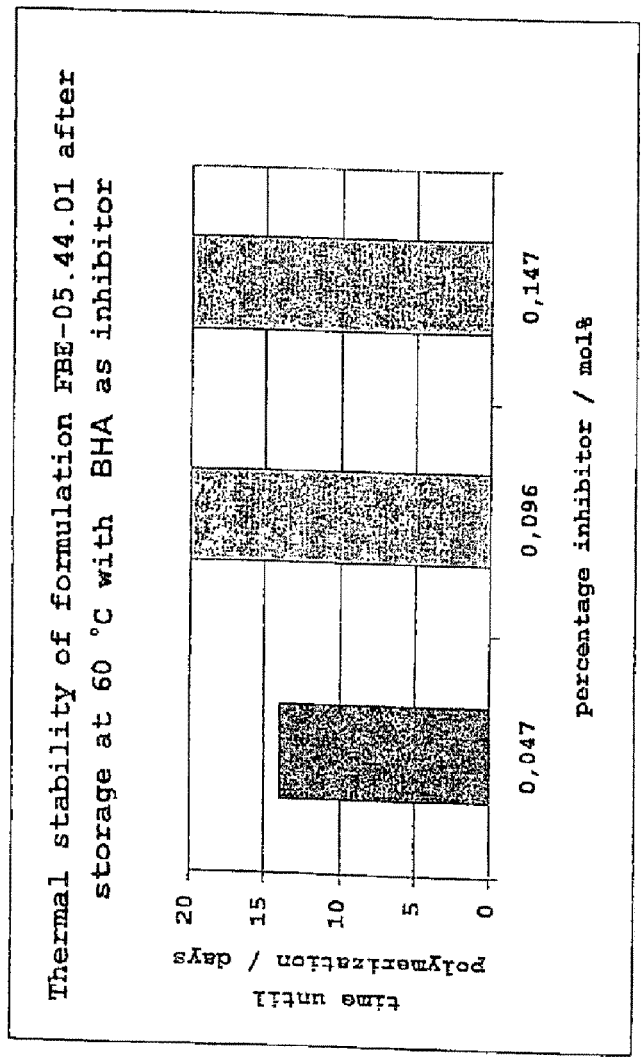
FIG. 6 shows the thermal stability of formulation FBE-05.44.01 after storage at 60° C. with tert.-Butylhydroxyanisole as inhibitor.

FIG. 6 shows the thermal stability 60 of formulation FBE-05.44.01 after storage at 60° C. with tert.-Butylhydroxyanisole as the inhibitor.

After 14 days at 60° C. all bottles were sliced open, the contents was investigated and filled in a new bottle, which was stored again at 60° C. The sample with 0.047 mol % showed after 14 days at 60° C. some pieces of gel, which were not detected before by shaking or by the examination with the pipette. After 20 days at 60° C. the bottles were again sliced open. No indication of polymerization for the samples containing 0.096 mol % and 0.147 mol % were found. The formulation with 0.047 mol % again contains some small pieces of gel.

Example 1

0.6945 g N,N'-Bisacrylamido-N,N'-diethyl-1,3-propane, 0.2315 g 3,(4),8,(9)-bis(acrylamido methyl)tricyclo-5.2.1.0$^{2,6}$ decane, 0.0595 g Ethyl 2-[12-dihydrogen phosphoryl-12,2-dioxamidecyl]acrylate, 0.0481 g 2-Acrylamido-2-methyl-propane-sulfonic acid, 0.0141 g camphor quinone, 0.0355 g bis(2,4,6-trimethylbenzoyl)-phenyl phosphine oxide, 0.0164 g dimethylamino benzoic acid ethyl ester and 0.003 g 2-tert-Butylhydroquinone were dissolved in a solvent mixture composed of 0.1800 g acrylic acid and 0.7200 g water.

The adhesive does not polymerise after storage for 20 days at 60° C.

Example 2

0.6940 g N,N'-Bisacrylamido-N,N'-diethyl-1,3-propane, 0.2313 g 3,(4),8,(9)-bis(acrylamido methyl)tricyclo-5.2.1.0$^{2,6}$ decane, 0.0595 g Ethyl 2-[12-dihydrogen phosphoryl-12,2-dioxamidecyl]acrylate, 0.0481 g 2-Acrylamido-2-methyl-propane-sulfonic acid, 0.0141 g camphor quinone, 0.0355 g bis(2,4,6-trimethylbenzoyl)-phenyl phosphine oxide, 0.0164 g dimethylamino benzoic acid ethyl ester and 0.0011 g 2-tert.-butyl-4-methoxyphenol were dissolved in a solvent mixture composed of 0.1800 g acrylic acid and 0.7200 g water.

The adhesive does not polymerise after storage for 20 days at 60° C.

Comparative Example 1

0.6931 g N,N'-Bisacrylamido-N,N'-diethyl-1,3-propane, 0.2310 g 3,(4),8,(9)-bis(acrylamido methyl)tricyclo-5.2.1.0$^{2,6}$ decane, 0.0594 g ethyl 2-[12-dihydrogen phosphoryl-12,2-dioxamidecyl]acrylate, 0.0480 g 2-Acryiamido-2-methyl-propane-sulfonic acid, 0.0141 g camphor quinone, 0.0354 g bis(2,4,6-trimethylbenzoyl)-phenyl phosphine oxide, 0.0164 g dimethylamino benzoic acid ethyl ester and 0.0026 g hydroquinone monomethyl ether were dissolved in a solvent mixture composed of 0.1800 g acrylic acid and 0.7200 g water.

The adhesive polymerises after storage for 1 day at 60° C.

Comparative Example 2

0.6882 g N,N'-Bisacrylamido-N,N'-diethyl-1,3-propane, 0.2294 g 3,(4),8,(9)-bis(acrylamido methyl)tricyclo-5.2.1.0$^{2,6}$ decane, 0.0590 g Ethyl 2-[12-dihydrogen phosphoryl-12,2-dioxamidecyl]acrylate, 0.0477 g 2-Acrylamido-2-methyl-propane-sulfonic acid, 0.0140 g camphor quinone, 0.0352 g bis(2,4,6-trimethylbenzoyl)-phenyl phosphine oxide, 0.0162 g dimethylamino benzoic acid ethyl ester and 0.0103 g 2,6-di-tert.-butyl-4-cresol were dissolved in a solvent mixture composed of 0.1800 g acrylic acid and 0.7200 g water. The adhesive polymerises after storage for 2 days at 60° C.

The invention claimed is:

1. A dental adhesive having a pH of at most 2, comprising an aqueous mixture containing:
    (i) one or more polymerizable monomers selected from the group consisting of N,N'-bisacrylamido-N,N'-diethyl-1,3-propane, 3,(4), 8, (9)-bis(acrylamido methyl) tricyclo-5.2.1.0$^{2,6}$ decane, ethyl 2-[12-dihydrogen phosphoryl-12,2-dioxamidecyl]acrylate, 2-Acrylamido-2-methyl-propane-sulfonic acid, and acrylic acid;
    (ii) optionally one or more organic or inorganic acids;
    (iii) a polymerization initiator selected from the group consisting of camphor quinone, bis(2,4,6-trimethylbenzoyl)-phenyl phosphine oxide, and dimethylamino benzoic acid ethyl ester; and
    (iv) a thermal polymerization inhibitor selected from the group consisting of tert.-butyl hydroquinone (TBHQ) and tert.-butyl hydroxyanisole (BHA);
    wherein the thermal polymerization inhibitor is present at a concentration such that the dental adhesive has a thermal stability at storage for at least 10 days at 60° C.; and
    wherein the dental adhesive is one-part self-etching and self-priming.

2. The dental adhesive according to claim 1, wherein the thermal polymerization inhibitor is tert.-butyl hydroquinone (TBHQ).

3. The dental adhesive according to claim 1, wherein the thermal polymerization inhibitor is contained in an amount of from 0.01 to 0.5 mol %.

4. The dental adhesive according to claim 1, wherein the aqueous mixture further contains an organic water soluble solvent selected from the group consisting of alcohols and ketones.

5. The dental adhesive according to claim 1, which contains the one or more polymerizable monomers in an amount of from 5 to 90 wt. %.

6. The dental adhesive according to claim 1, which further contains an inorganic filler, an organic filler, or both.

7. The dental adhesive according to claim 1, wherein the aqueous mixture further contains an organic water soluble solvent selected from the group consisting of ethanol, propanol, butanol, acetone, and methyl ethyl ketone.

8. The dental adhesive according to claim 1, wherein the polymerization initiator is camphor quinone.

9. The dental adhesive according to claim 1, wherein the thermal polymerization inhibitor is tert.-butyl hydroxyanisole (BHA).

10. The dental adhesive according to claim 1, wherein the concentration of the thermal polymerization inhibitor is less than or equal to about 0.147 mol %.

11. A method of using a thermal polymerization inhibitor, the method comprising:
    mixing the thermal polymerization inhibitor in an aqueous mixture to form a dental adhesive, the thermal polymerization inhibitor being selected from the group consisting of tert.-butyl hydroquinone (TBHQ) and tert.-butyl hydroxyanisole (BHA), the thermal polymerization inhibitor being present at a concentration such that the dental adhesive has a thermal stability at storage for at least 10 days at 60° C., the aqueous mixture containing:
    (i) one or more polymerizable monomers selected from the group consisting of N,N'-bisacrylamido-N,N'-diethyl-1,3-propane, 3, (4),8, (9)-bis(acrylamido methyl)tricyclo-5.2.1.0$^{2,6}$ decane, ethyl 2-[12-dihydrogen phosphoryl-12,2-dioxamidecyl]acrylate, 2-Acrylamido-2-methyl-propane-sulfonic acid, and acrylic acid;
    (ii) optionally one or more organic or inorganic acids, and
    (iii) a polymerization initiator selected from the group consisting of camphor quinone, bis(2,4,6-trimethylbenzoyl)-phenyl phosphine oxide, and dimethylamino benzoic acid ethyl ester; and
    wherein the dental adhesive is one-part self-etching, self-priming and has a pH of at most 2.

12. The method according to claim 11, wherein the concentration of the thermal polymerization inhibitor is less than or equal to about 0.147 mol %.

* * * * *